US009656002B2

(12) United States Patent
Castro et al.

(10) Patent No.: US 9,656,002 B2
(45) Date of Patent: May 23, 2017

(54) METHODS TO INCREASE FRACTURE RESISTANCE OF A DRUG-ELUTING MEDICAL DEVICE

(71) Applicant: Abbott Cardiovascular Systems Inc., Santa Clara, CA (US)

(72) Inventors: Dan Castro, Santa Clara, CA (US); Yunbing Wang, Sunnyvale, CA (US)

(73) Assignee: ABBOTT CARDIOVASCULAR SYSTEMS INC., Santa Clara, CA (US)

( * ) Notice: Subject to any disclaimer, the term of this patent is extended or adjusted under 35 U.S.C. 154(b) by 95 days.

(21) Appl. No.: 14/054,722

(22) Filed: Oct. 15, 2013

(65) Prior Publication Data

US 2014/0044860 A1 Feb. 13, 2014

Related U.S. Application Data

(63) Continuation of application No. 12/490,248, filed on Jun. 23, 2009, now Pat. No. 8,597,716.

(51) Int. Cl.
| | | |
|---|---|---|
| *A61L 31/08* | (2006.01) | |
| *A61F 2/91* | (2013.01) | |
| *A61F 2/915* | (2013.01) | |
| *A61F 2/06* | (2013.01) | |
| *B05D 1/34* | (2006.01) | |
| *A61F 2/95* | (2013.01) | |

(52) U.S. Cl.
CPC .............. *A61L 31/08* (2013.01); *A61F 2/91* (2013.01); *A61F 2/915* (2013.01); *A61F 2/06* (2013.01); *A61F 2002/91558* (2013.01); *A61F 2002/91566* (2013.01); *A61F 2002/91575* (2013.01); *A61F 2002/9522* (2013.01); *A61F 2240/001* (2013.01); *A61F 2250/0067* (2013.01); *B05D 1/34* (2013.01); *Y10T 29/49913* (2015.01)

(58) Field of Classification Search
CPC .. A61F 2/06; A61F 2/48; B21D 39/00; B05D 1/34
USPC .......................... 623/1.24, 1.42, 1.11; 29/516
See application file for complete search history.

(56) References Cited

U.S. PATENT DOCUMENTS

| | | |
|---|---|---|
| 4,977,901 A | 12/1990 | Ofstead |
| 5,836,965 A | 11/1998 | Jendersee et al. |
| 5,913,871 A | 6/1999 | Werneth et al. |
| 5,976,181 A | 11/1999 | Whelan et al. |

(Continued)

FOREIGN PATENT DOCUMENTS

| | | |
|---|---|---|
| EP | 0 787 020 | 5/1996 |
| EP | 1 226 798 | 5/2000 |

(Continued)

OTHER PUBLICATIONS

International Search Report for PCT/US2010/039226, mailed Aug. 30, 2010, 6 pgs.

(Continued)

*Primary Examiner* — Dah-Wei D Yuan
*Assistant Examiner* — Andrew Bowman
(74) *Attorney, Agent, or Firm* — Squire Patton Boggs (US) LLP

(57) ABSTRACT

Methods for increasing the fracture resistance of a polymer stent's drug-polymer coating and scaffolding including applying a coating and crimping using techniques that increase the resistance to fracture in the coating layer and scaffolding and scaffolding.

15 Claims, 4 Drawing Sheets

(56) References Cited

U.S. PATENT DOCUMENTS

| | | |
|---|---|---|
| 5,980,972 A | 11/1999 | Ding |
| 6,063,092 A | 5/2000 | Shin |
| 6,629,350 B2 | 10/2003 | Motsenbocker |
| 6,745,445 B2 | 6/2004 | Spilka |
| 6,863,683 B2 | 3/2005 | Schwager et al. |
| 7,010,850 B2 | 3/2006 | Hijlkema et al. |
| 7,316,148 B2 | 1/2008 | Asmus et al. |
| 7,761,968 B2 | 7/2010 | Huang et al. |
| 7,951,185 B1 | 5/2011 | Abbate et al. |
| 8,002,817 B2 | 8/2011 | Limon et al. |
| 8,003,158 B2 | 8/2011 | Jow |
| 8,123,793 B2 | 2/2012 | Roach et al. |
| 8,182,890 B2 | 5/2012 | Zheng et al. |
| 8,261,423 B2 | 9/2012 | Jow et al. |
| 2002/0138135 A1* | 9/2002 | Duerig et al. ............... 623/1.24 |
| 2002/0143382 A1 | 10/2002 | Hijlkema et al. |
| 2004/0078953 A1 | 4/2004 | Spilka |
| 2004/0106973 A1 | 6/2004 | Johnson |
| 2004/0138731 A1 | 7/2004 | Johnson |
| 2005/0118344 A1 | 6/2005 | Pacetti |
| 2005/0119720 A1 | 6/2005 | Gale et al. |
| 2005/0143752 A1 | 6/2005 | Schwager et al. |
| 2005/0203605 A1 | 9/2005 | Dolan |
| 2006/0047336 A1 | 3/2006 | Gale et al. |
| 2006/0287715 A1 | 12/2006 | Atladottir et al. |
| 2007/0006441 A1 | 1/2007 | McNiven et al. |
| 2007/0204455 A1 | 9/2007 | Knott et al. |
| 2007/0208416 A1 | 9/2007 | Burpee et al. |
| 2007/0271763 A1 | 11/2007 | Huang et al. |
| 2007/0281073 A1 | 12/2007 | Gale et al. |
| 2007/0282433 A1 | 12/2007 | Limon et al. |
| 2007/0289117 A1 | 12/2007 | Huang et al. |
| 2008/0016668 A1 | 1/2008 | Huang et al. |
| 2008/0033523 A1 | 2/2008 | Gale et al. |
| 2008/0033524 A1 | 2/2008 | Gale |
| 2008/0147164 A1 | 6/2008 | Gale et al. |
| 2008/0275537 A1 | 11/2008 | Limon |
| 2009/0001633 A1 | 1/2009 | Limon et al. |
| 2009/0087541 A1 | 4/2009 | Jow et al. |
| 2009/0088829 A1* | 4/2009 | Wang ..................... A61F 2/958 623/1.11 |
| 2009/0105800 A1* | 4/2009 | Sabaria ..................... 623/1.11 |
| 2010/0004735 A1 | 1/2010 | Yang et al. |
| 2010/0025894 A1 | 2/2010 | Kleiner et al. |
| 2010/0063571 A1 | 3/2010 | Roach et al. |
| 2010/0241220 A1* | 9/2010 | McClain et al. ............. 623/1.42 |
| 2010/0323091 A1 | 12/2010 | Castro et al. |
| 2011/0270383 A1 | 11/2011 | Jow et al. |
| 2011/0271513 A1 | 11/2011 | Wang |
| 2012/0010693 A1 | 1/2012 | Van Sciver |
| 2012/0042501 A1 | 2/2012 | Wang et al. |
| 2012/0079706 A1 | 4/2012 | Knott et al. |
| 2012/0271396 A1 | 10/2012 | Zheng et al. |

FOREIGN PATENT DOCUMENTS

| | | |
|---|---|---|
| EP | 1 295 570 | 7/2002 |
| EP | 2 029 052 | 3/2003 |
| WO | WO 99/55406 | 11/1999 |
| WO | WO 02/102283 | 8/2002 |
| WO | WO 2005/053937 | 6/2005 |
| WO | WO 2006110861 | 10/2006 |
| WO | WO 2007/006562 | 1/2007 |
| WO | WO 2007/146354 | 12/2007 |
| WO | WO 2008/033621 | 3/2008 |
| WO | WO 2010/151497 | 12/2010 |

OTHER PUBLICATIONS

Japan Patent Office, Notice of Reasons for Rejection with English translation for application No. 2015-076030, dispatched Mar. 22, 2016.

* cited by examiner

METHODS TO INCREASE FRACTURE RESISTANCE OF A DRUG-ELUTING MEDICAL DEVICE

BACKGROUND OF THE INVENTION

Field of the Invention

The present invention relates to drug-eluting medical devices; more particularly, this invention relates to processes for making a drug-eluting, polymer-based medical device.

Background of the Invention

Strict pharmacological and good mechanical integrity of a drug eluting medical device are required to assure a controlled drug release. Significant technical challenges exist when developing an effective and versatile coating for a drug eluting medical device, such as a stent.

The art recognizes a variety of factors that might play a significant role in a stent coating's ability to retain its integrity when subjected to external loadings, such as crimping and balloon expansion. According to the art, many of these factors are not fully understood, nor their significance fully appreciated. To the inventor's knowledge, the art has only been able to characterize the mechanisms of action as pertains to coating integrity at a theoretical level. A discovery of a relationship between the material, process used to coat, deformation of the stent in relation to that of the coating, etc. that might reduce the inherent uncertainty in this field, however, has yet to be articulated. As will be appreciated, the fracture mechanics for a coating is a highly non-linear problem that cannot be reduced down to a few variables.

Nevertheless, the art has tried to develop a methodology capable of reducing the fracture problem down to a few unknowns—e.g., choosing a temperature range, a crimping protocol, and a polymer having the desired elastic properties as a function of the stent and clinical/therapeutic objectives. For example, attempts have been made to predict interlaminar shear, crack propagation and related structural-mechanical behavior of a coating when subjected to an external load using a finite element-based analytic approach. To the inventors' knowledge, however, none of these efforts have proven successful, at least to the extent that their results might enable those in the medical device field to predict with any useful degree of certainty whether a particular drug-eluting stent will suffer from cracks, peeling, etc. in its coating absent device-specific testing.

In light of the foregoing, there is a need for a method that improves the integrity or resilience of a drug-polymer coating carried by a polymer-based medical device, such as a polymer stent, when the medical device is subjected to external loads. It is important to avoid cracking and/or peeling of a drug-polymer coating. Potentially, such coating damage during stent radial expansion/contraction can cause severe thrombogenic response after stent implantation and compromise control of the drug dosage and/or rate of release of the drug-eluting stent.

SUMMARY OF THE INVENTION

The invention improves upon the art by providing a method for making a drug eluting polymeric stent including the steps of forming a stent body from a polymer tube having a diameter about equal to the maximum deployed stent diameter, reducing the stent diameter to an intermediate diameter, applying a drug-polymer coating to the stent, and then crimping the stent down to the delivery or minimum stent diameter. A significant reduction in the instances of cracking/peeling has been observed using this method.

Methods according to the invention may be practiced without substantially affecting, compromising or altering other prior established/confirmed functionality of the drug-eluting stent, such as the integrity of the polymer scaffolding which receives the coating, the drug release rate, the rate of biodegradation, etc. According to this aspect, the invention helps to simplify the development process. For example, suppose it becomes necessary, after all stent functions have been verified through clinical trials, to increase the deployed diameter while maintaining the same stowed diameter, or decrease the stowed diameter. If cracking/peeling then appears when the stent is expanded, i.e., as related to an increased range of deformation required of the stent scaffolding and coating; there is an important, yet heretofore unfulfilled need in the art to address this type of problem without changing a polymer, a stent pattern, the coating thickness, ratio of drug to polymer, etc. While in some cases it may become inevitable that a drug-eluting stent needs to be modified substantially to address a cracking problem in the coating, the invention provides methods that can, in some cases, obviate this need, thereby avoiding the need for additional clinical trials.

Unless otherwise indicated, the terms "stowed diameter" and "deployed diameter" carry the same meaning as crimped diameter and deployed diameter in U.S. Pub. 2008/0275537.

According to one aspect of invention, a method for crimping a drug-eluting polymer stent to avoid crack propagation in the drug-polymer coating includes the step of applying a coating by a spraying technique after reducing the stent diameter to an intermediate diameter, followed by baking the polymer coating and scaffolding to increase fracture resistance in the coating and scaffolding. The method may further include a final crimping step including four stages. After each reduction in diameter a relaxation period is used to relieve stress/strain in the coating and scaffolding.

According to another aspect of invention, a baking step is used to anneal material following crimping and coating. After a final coating weight is reached, the stent is placed in an oven for between 15 minutes and one hour at about 50 degrees Celsius. The baking period may be longer, e.g., 2 hours, when a suitable baking temperature is selected for this length of time. This baking step increases the fracture resistance of the drug-eluting polymer stent. It is believed that during the baking period the internal stress concentration is reduced, thereby increasing the fracture resistance. In addition, it is proposed that the shear resistance of the binding, transition, or intermediate layer between the semi-crystalline scaffolding polymer and amorphous (or more amorphous) coating polymer could be increased by potentially allowing the two materials to bind together, which improves fracture resistance.

Another aspect of the invention is a method for increasing fracture resistance including a diameter reduction step of about 50-80%, the diameter reduction step performed on a polymer scaffolding, e.g., one having a W-shaped closed cell pattern and strut displacement between crimped and deployed diameters of above 130 degrees about a hinge element, a coating process including depositing a drug-polymer mixed with a solvent in an amount of between about 90-98% by weight solvent, an annealing step of about 15-60 min at a relaxation temperature of about 5-20 degrees below a glass transition temperature for an amorphous and semi crystalline polymer, and a crimping process including a three part diameter reduction at a relaxation temperature of between 5-20 degrees below a glass transition temperature for an amorphous polymer (coating) and semi crystalline polymer (scaffolding).

A method according to the invention may also include building a drug-eluting polymer stent with a higher-than-deployed initial diameter (i.e., greater than the design deployed diameter for the vessel type), followed by a diameter reduction, then a coating step to minimize crack propagation in the drug-polymer coating. Wherein the stent is capable of being reduced in size to about 40% of its starting size without crack propagation in the coating. The coating thickness may be about 2-10 microns and the ratio of drug to polymer coating is about 1:1 to 1:3.

According to another aspect of invention a method for crimping a drug-eluting polymer includes reducing the stent diameter to a crimped diameter and loading the stent having the crimped diameter onto a delivery catheter, wherein the stent is a drug-eluting polymer stent having a drug to polymer loading ratio of 1:1 to 1:3 and the ratio of deployed to crimped diameters is between 2 and 5.

According to another aspect of invention, there is a method of making a drug-eluting stent having a PDLA to drug ratio of 1:1 for the coating including the steps of making a stent body having a first diameter, applying the drug-polymer coating, then reducing the stent size to a second diameter, wherein the ratio of first diameter to second diameter is about 3:1.

INCORPORATION BY REFERENCE

All publications and patent applications mentioned in this specification are herein incorporated by reference to the same extent as if each individual publication or patent application was specifically and individually indicated to be incorporated by reference, and as if each said individual publication or patent application was fully set forth, including any figures, herein.

BRIEF DESCRIPTION OF THE DRAWINGS

FIG. 3 shows a scaffolding geometry in an expanded or deployed state. FIG. 4 shows a portion of a W-shaped element of the scaffolding geometry of FIG. 3 when the scaffolding is configured in its stowed or crimped diameter state.

DETAILED DESCRIPTION OF EMBODIMENTS

Figure 1:
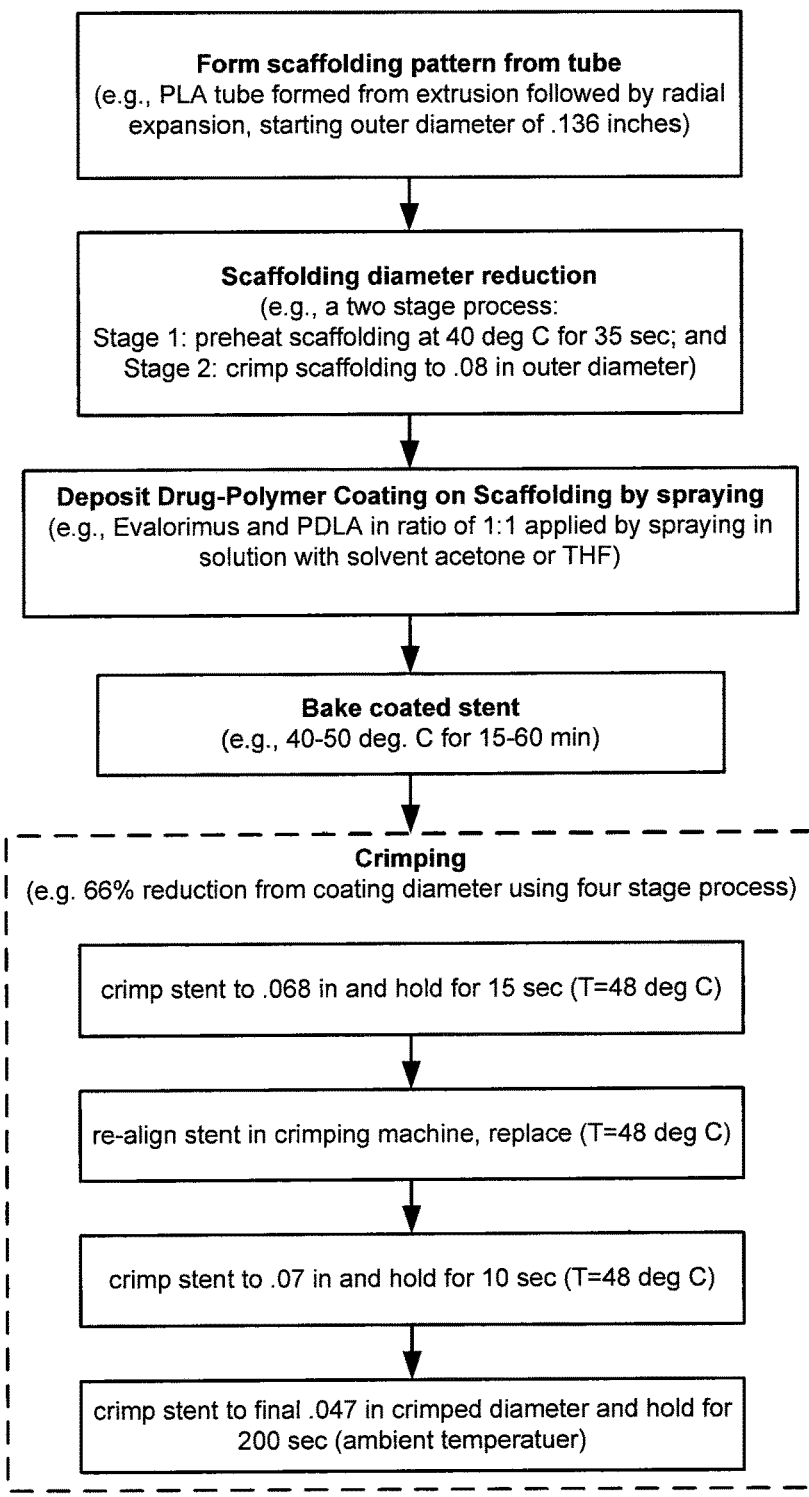
FIG. 1 is a flowchart depicting a preferred implementation of a drug-eluting stent manufacturing process according to the invention.

According to a preferred embodiment the polymer poly (D, L-lactic acid) (hereinafter "PDLA") carries the drug in the coating. PDLA is an amorphous polymer, i.e., lacking any defined crystalline pattern. As such, PDLA tends to provide more favorable fracture resistance properties over a polymer that has a semi crystalline, or crystalline structure. The polymer for the scaffolding may be PLLA or Poly (lactide-co-glycolide) (PLGA). Any composition between 0 and 100% of lactide, in particular, a range of 80/20 to 90/10 of lactide/glycolide on a molar basis, or a range of 93/7 to 97/3 of lactide/glycolide on a molar basis may be used for a PLGA scaffolding polymer.

The fracture elongation of PDLA has been measured to be about 5%. "Fracture elongation" is meant to mean the percentage elongation of the material before the onset of significant cracking/peeling. This quantity may be measured by a tensile test known as the dumb bell test, as is known in the art. Unfortunately, there is no linear or direct relationship between the percentage of fracture elongation for PDLA and a PDLA coating's ability to withstand cracking and peeling for a particular stent drug-eluting stent design. For example, it was found that the capacity of PDLA-drug coating in the disclosed embodiments to resist cracking was not directly related to its 5% measured fracture elongation, even when one takes into account the presence of a drug in the polymer, e.g., a ratio of 1:1 drug to polymer. As such, it was found not possible to make accurate predictions based on this quantity alone. According to the invention, when other factors (other than the properties of the polymer) are also taken into consideration, results can be better predicted and more widely applied. These factors include the stent geometry, material properties, method of application of the drug-polymer coating, drug-polymer ratio, coating weight, the crimping process used and the temperature used when material is worked between or during processing steps.

The fracture resistance of an applied drug-polymer coating can vary significantly from that of a polymer without contaminants, or when the drug-polymer coating is applied by one method verses another. For example, the fracture characteristics of a coating applied by, e.g., dipping, can differ from a coating applied by spraying the drug-polymer dissolved in a solvent. In a preferred embodiment a drug-polymer coat is applied by spraying about 13 coats of a low weight solution, which includes PDLA and the drug (Everolimus) dissolved in the solvent (acetone or THF). In one embodiment, the drug and PDLA are mixed in a ratio 1:1.

A greater or lesser percentage of drug in the coating can affect fracture resistance. Switching to a higher percentage of polymer to drug, e.g. 2:1, 3:1, might improve the fracture resistance significantly, while a lower percentage may reduce the fracture resistance. So, in order to arrive at the same drug loading while improving the fracture resistance one might choose to apply a solution that has more polymer than drug with a resulting thicker coating. For example, if a ratio of 2:1 (i.e., 2/3 polymer 1/3 drug in the coating) were chosen over the preferred 1:1, the thickness of the coating would be about 4 microns instead of 2 microns in order to have the same drug loading. Selecting a different polymer, other than PDLA, may also provide higher fracture resistance for the coating. It will be appreciated that these types of solutions can alter the drug release profile for the stent. The choice of a particular coating, therefore, requires consideration of the effects this new coating, or changed drug-polymer ratio or coating thickness will have on the desired drug release profile.

For a spray method of application of the coating, the fracture resistance may also be affected by the percentage of solvent in each coat, and/or solvent remaining in a previous coat when a subsequent coating is applied, and/or solvent remaining after the final coating weight is reached. In one embodiment, a coating thickness of about 3 microns is formed when 100% of the coating weight is reached. The final coating weight is arrived at by applying several spray cycles of a solution having 2% of the final coating weight, followed immediately by an in-process drying step. In this example, it has been found that only about 2% of the final coating weight is solvent that was not removed. The coated scaffolding is then baked to remove the remaining solvent. If a higher coating weight were applied per spray cycle, for example, then the fracture characteristics of the coating may change because the solvent's effect on the inter laminar stress/strain characteristics between the coating and scaffolding may be different (due to the presence of a higher concentration of solvent remaining before it can be removed by a drying or baking step).

In one embodiment, a 3×18 stent exhibiting improved fracture toughness when made in accordance with aspects of the invention, was coated by applying 13 passes of a drug-polymer dissolved in a solvent. The coating weight per pass was about 15 micro-grams (7.5 micro-grams of drug and 7.5 micro-grams of polymer) or 7.77 micro-grams per square centimeter per pass.

One of ordinary skill will appreciate that once a desired release profile is reached by a particular selection of drug to polymer, coating thickness, and method of application, it may not be desirable to alter these properties or method of application in order to address a cracking, peeling, or flaking problem (due to the challenges faced when arriving at a process for producing a desired release profile, it is often preferred to not alter these parameters when dealing with a problem like cracking). In these cases, the skilled artisan will appreciate that a solution to a cracking/peeling problem which alters properties of the coating, and therefore potentially the drug release properties, does not solve one of the needs in the art addressed by the invention. It is preferred to find a solution which is least likely to affect a drug release profile.

According to some embodiments, the invention is directed to a method for improving the fracture resistance of drug-polymer coating on a polymer scaffolding, as opposed to a metal scaffolding. A polymer scaffolding introduces added complexity not present in a metal scaffolding. These complexities are discussed more fully in US. Publication 2008/0275537. According to one aspect of the invention a polymer scaffolding is formed from a tube corresponding to the deployed diameter as this allows the polymer to be formed in a semi-crystalline shape having improved hoop strength. The drug-polymer coat is applied after the scaffolding is reduced in diameter by a diameter reduction step, as discussed in greater detail, below.

A metal (as opposed to polymer) scaffolding may optionally be cut from a tube having a diameter corresponding to an intermediate stage of expansion because there isn't the same concern of fracture due to expansion beyond the formed tube size. Hence, to address a fracture concern in the coating, there are more options available when a metal stent is used. Additionally, because metal can be polished before a coating is applied (thereby reducing the surface roughness) and is less likely to possess micro-cracks or other imperfections at the surface, it will be appreciated that coating fracture resistance for a drug-eluting metal stent may be higher because surface imperfections are fewer. With fewer surface imperfections there should be greater resistance to fracture in the coating when the surface deforms during crimp or balloon expansion.

Since fracture resistance is a critical parameter effecting the usability of a polymer scaffolding, along with minimizing recoil and high stiffness, the effects of application of a solvent applied to its surface (when a coating is applied) needs to be considered. It is important to avoid using a solvent that dissolves the polymer in the scaffolding to such an extent that the mechanical properties of the scaffolding (stiffness, strength) begin to degrade. However, it has also been found that when dissolving the scaffolding polymer in a limited amount close to its outer surface, this solvent-polymer interaction can be beneficial to maintaining integrity of the coating when the stent is expanded/contracted.

When a drug-polymer dissolved in a solvent is applied to a polymer scaffolding surface, the solvent will, to some extent, interact with the scaffolding polymer at the surface. This interaction can, of course, be more significant when a greater percentage of the solution is solvent and depending on the solvent used and material in the scaffolding. In one embodiment about 90-98% of the solution sprayed on the surface of the PLA scaffolding is the solvent acetone or THF.

It is important that the solvent be removed from the surface of the stent a controlled rate, because the solvent's presence on the surface can affect things like the integrity of the scaffolding, the properties of the polymer in the coating and the release properties of the drug. Solvent, when in contact with the scaffolding layer, can cause swelling of the polymer material forming the scaffolding surface. When controlled properly, this swelling can be beneficial as a means for creating a kind of binding layer between the coating polymer and scaffolding. However, the presence of solvent can also adversely affect the fracture resistance of the coating.

One preferred aspect of the invention pertains to a baking step for the coating. After the final coating weight is reached, the stent is placed in an oven for between 15 minutes and one hour at about 50 degrees Celsius. It has been found that the baking step increases the fracture resistance of the drug-eluting polymer stent. While not wishing to be tied to any particular theory, it is believed that during the baking period, residual stress concentrations in the drug-polymer coating, polymer scaffolding and transition layer are at least partially reduced and therefore increased fracture resistance results. In addition, it might be possible that the shear resistance of the binding or transition layer between the semi-crystalline scaffolding polymer and amorphous (or more amorphous) coating polymer could potentially increase, which improves fracture resistance.

The temperature and rate deformation of a stent during a crimping stage processing of the stent can influence the integrity of the coating, as well as the integrity of the scaffolding. A more rapid, or slower, incremental crimping process, conducted at selected temperatures, i.e., fewer/more steps at higher/lower temperatures, influences the amount of relaxation of internal stress/strain in the scaffolding material. The crimping method can also affect the integrity of the drug-polymer coating. According to embodiments of the invention a four-part crimping process at about 40 degrees (about 10 degrees below the glass transition temperature of PDLA) is used.

The beneficial effects to the scaffolding by the four step process can also provide benefits to the coating. When the stent is incrementally reduced in size at a temperature that allows internal stress/strain to be relieved, this relaxation period can also serve to work out any associated stress/strain at the interface between the coating and the scaffolding surface, such as at the binding or transition layer discussed earlier. As such, the method used to crimp the stent down to its stowed or crimped diameter also affects the coating's ability to resist cracking and peeling when expanded or contracted.

Stress/strain behavior at the interface of the coating layer and surface of the scaffolding can differ significantly depending on the surface of the stent where the coating is applied. Hence, the stent geometry is also a factor to take into consideration. Scaffolding, which expand/contract radially by working certain members greater than others, should therefore also produce higher stress concentrations in the coating at or near these same areas. Whether the stresses are sufficient to cause fracture in the coating, however, is not readily deducible from a stent pattern. Some stent geometries may be more susceptible to cracking in the coating than others, despite good performance, i.e., no fracture problems, in the polymer scaffolding between deployed and stowed diameters. The exact relationship between stress/strain in the stent and the transference of these loads into inter-laminar coating stresses is not fully understood. Therefore, a cracking/peeling problem cannot, in general, be anticipated or an adequate solution known in advance for an arbitrary stent geometry, or defined stress/strain distribution obtained through a mathematical model of the scaffolding.

Figure 2:
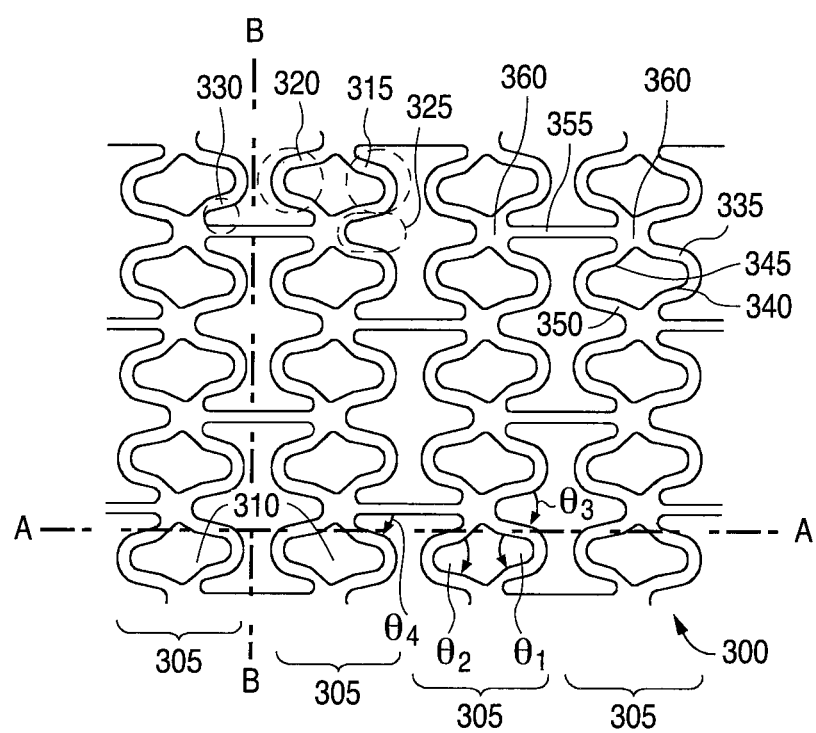
FIG. 2 is a projected view of a first scaffolding geometry. This figure shows the scaffolding geometry in its deployed or expanded diameter state.

A PDLA-drug coating was applied to a stent scaffolding 700 described in U.S. Publication 2008/0275537 when it has its fully deployed diameter. The stent was then compressed down to its stowed diameter and then expanded again to its deployed diameter by a catheter balloon. Cracks and peeling appeared in several places in the coating. In the case of the scaffolding 300 shown in FIG. 3 of U.S. Publication 2008/0275537, reproduced here as FIG. 2, a similar cracking/peeling problem did not occur for the same material in the scaffolding, drug-polymer coating layer and ratio of deployed to stowed diameter (both stents had a deployed to stowed diameter ratio of about 2.5). It is believed that the difference might be explained in terms of the magnitude of the angle through which struts turn about hinge points.

Figure 3:
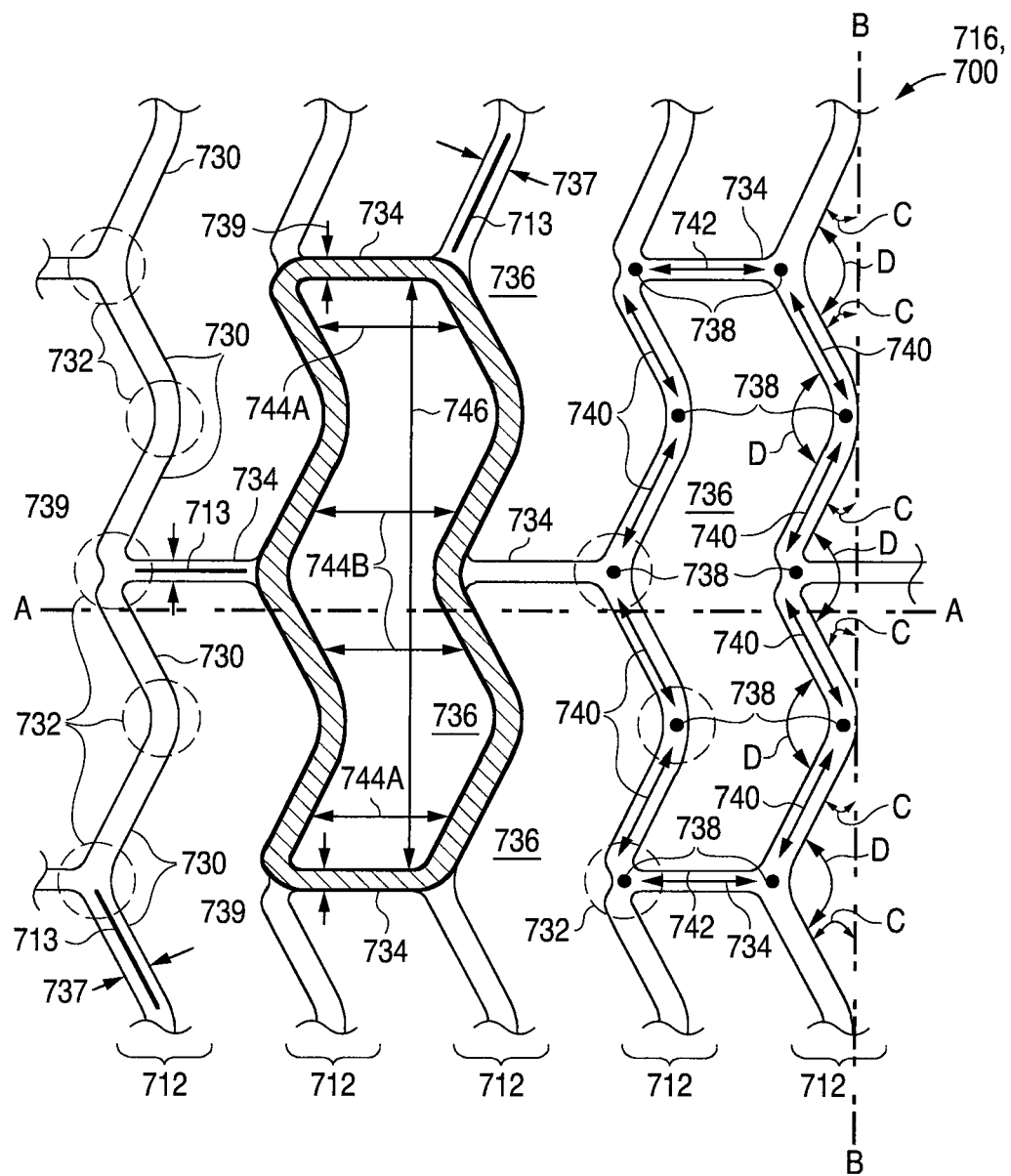
FIGS. 3-4 are projected views of a second scaffolding geometry.
Figure 4:
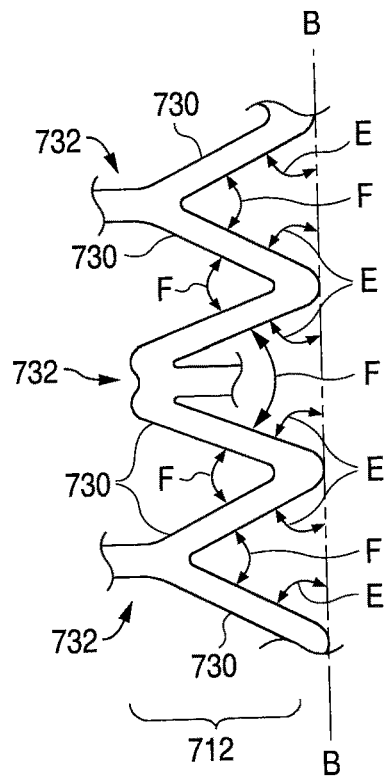
Figure 5:
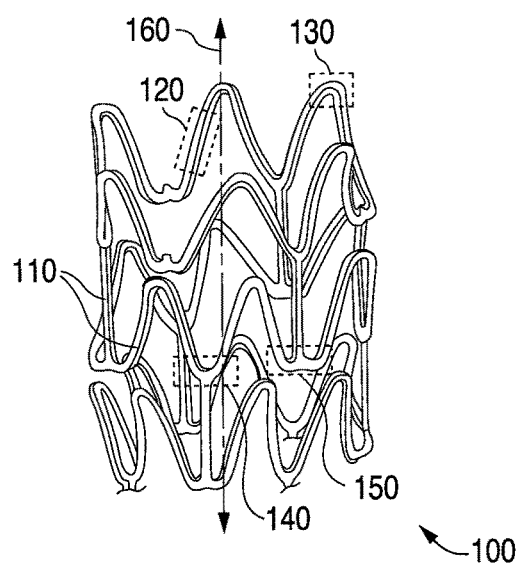
FIG. 5 is an isometric view of a third scaffolding geometry.

Referring to FIGS. 6-7 of U.S. Publication 2008/0275537, reproduced here as FIGS. 3-4, the ring elements 732 of a ring 712 forms an angle F when the scaffolding is compressed, and an angle D (greater than F) when initially cut from the PLLA tube, i.e., uncompressed state. In one embodiment, the angle D is greater than 100 degrees and preferably between 124 degrees and 130 degrees. As can be appreciated by comparing FIG. 2 with FIG. 3, when compressed the member 730 will rotate through a greater angle about its hinge point 738 than the corresponding members associated with structure 320/315 (angles $\Theta_1$, $\Theta_2$, and $\Theta_3$) for the same ratio of deployed to stowed diameters. FIG. 5 shows a stent geometry according to another embodiment.

Referring once again to FIG. 3, the scaffolding includes link struts 734 connecting the rings 712 together. The link struts 734 are oriented parallel or substantially parallel to line A-A. The ring struts 730, hinge elements 732, and link struts 734 define a plurality of W-shaped closed cells 736. The boundary or perimeter of one W-shaped cell 736 is darkened in FIG. 3 for clarity. The W-shapes appear rotated 90 degrees counterclockwise. Each of the W-shaped cells 736 is immediately surrounded by six other W-shaped cells 736, meaning that the perimeter of each W-shaped cell 736 merges with a portion of the perimeter of six other W-shaped cells 736. Stated another way, each W-shaped cell 736 abuts or touches six other W-shaped cells 736.

The perimeter of each W-shaped cell 736 includes eight of the ring struts 730, two of the link struts 734, and ten of the hinge elements 732. Four of the eight ring struts form a proximal side of the cell perimeter and the other four ring struts form a distal side of the cell perimeter. The opposing ring struts on the proximal and distal sides are parallel or substantially parallel to each other.

As shown in FIG. 3, the interior space of each W-shaped cell 736 has an axial dimension 744 parallel to line A-A and a circumferential dimension 746 parallel to line B-B. The axial dimension 744 is constant or substantially constant with respect to circumferential position. That is, axial dimensions 744A adjacent the top and bottom ends of the cells 736 are the same or substantially the same as axial dimensions 744B further away from the ends. In the illustrated embodiment of FIG. 3, axial and circumferential dimensions 744 and 746 are the same among the W-shaped cells 736.

FIG. 4 shows a portion of one ring 712 in two different deformed configurations. In FIG. 4, the ring 712 has been radially compressed to a diameter less than its initial outer diameter, such as when the stent is crimped onto a catheter. During such compression, the ring struts 730 pivot about the hinge elements 732 so that the ring struts 730 fold toward each other and become oriented at an angle E relative to the reference plane represented by line B-B. Angle E is greater than corresponding angle C in FIG. 3 which shows rings 712 in the non-deformed configuration. Also, the ring struts 730 are oriented at an interior angle F relative to each other. Angle F is less than corresponding angle D in FIG. 3. In a preferred embodiment a polymer stent is subjected to a diameter reduction step suitable for the polymer scaffolding. The polymer-drug coating is then applied. After which the stent is crimped down to its stowed or crimped diameter using a multi-step process. It was discovered that for a polymer-drug coating ratio of about 1:1, method of application of the coating by spraying the drug-polymer dissolved in a solvent on the polymer scaffolding, sharply reduced instances of cracking and peeling. One of ordinary skill will appreciate, in light of this disclosure, that the methods of the invention may be readily adapted to other combinations of coating and scaffolding not limited to the preferred embodiment, without departing from the scope of invention.

One benefit to the diameter reduction step is that a more consistent coating is applied for a spraying technique. With a reduced diameter an abluminal and luminal surface are brought closer together, which results in more similar spray concentrations striking the surface at the same time. If a more similar spray concentration is striking the surface, a more uniform coating can result.

With reference to FIG. 1, in the example that follows a stent scaffolding 700 has a maximum diameter that was about 2.5 times its stowed or fully crimped diameter. The final drug-polymer coating on the stent has a coating thickness of about 3 microns. The ratio of drug to polymer was about 1:1 and the coating is applied by a spraying technique in which the drug-polymer is dissolved in a solvent. A baking step and four-stage crimping is also used.

The scaffolding 700 (FIG. 3) was formed from an extruded tube of PLLA radially deformed to about the maximum diameter expected for the scaffolding during clinical use, which forming process is described in greater detail in U.S. Pub. No. 2008/275537. The radial deformation step produces a radially oriented, semi-crystalline structure that exhibits increased stiffness and reduced recoil when cyclic, radial loads are applied to the scaffolding. A laser is used to form the scaffolding pattern from the tube. Preferably, the tube diameter is larger than a deployed or expanded diameter for the stent when implanted in the vessel. This is to minimize the possibility that the physician will over-expand the stent to a diameter larger than the tube diameter during use. Expansion of a stent beyond the initial tube diameter increases the likelihood of crack propagation in the coating.

A scaffolding outer diameter may be designated by where it is expected to be used, e.g., a specific location or area in the body. The outer diameter, however, is usually only an approximation of what will be needed during the procedure.

For instance, there may be extensive calcification that breaks down once a therapeutic agent takes effect, which can cause the stent to dislodge in the vessel. Further, since a vessel wall cannot be assumed as circular in cross-section, and its actual size only an approximation, a physician can choose to over-extend the stent to ensure it stays in place. For this reason, it is preferred to use a tube with a diameter larger than the expected deployed diameter of the stent.

In one embodiment the ratio of deployed to fully crimped diameter is about 2.5. In this embodiment, the crimped diameter corresponds to an outer diameter that is only about 40% of the starting diameter. Hence, when deployed the drug eluting stent is expected to increase in size up to about 2.5 times its stowed or crimped diameter size. In other embodiments the difference in diameter size between the stowed diameter and deployed diameter may be up to 4.0, or the deployed diameter is between 250-400% greater than the crimped diameter for a balloon expanded polymer scaffolding.

According to one aspect of the invention a method for increased fracture resistance is applied to a scaffolding having a pair of struts forming a part of a closed cell spaced at an angle of greater than 100 degrees, or between 124 and 132 degrees from an opposing strut. An example of such a scaffolding pattern is depicted in FIG. 3. The closed cell pattern has W-shaped elements formed by interconnected struts 730. Referring to FIGS. 3-4, a hinge point is the ring elements 732 of a ring 712. The angle F is formed when the scaffolding is compressed, and an angle D (greater than F) when deployed.

After the scaffolding is formed, a two-stage diameter reduction step is performed. According to a preferred embodiment, a PLLA scaffolding is subjected to a temperature of 48 deg. C. for 35 sec, then a crimping machine reduces its diameter about 60%, e.g., from a 0.136 in diameter to a 0.08 diameter. The temperature is maintained 48 deg. C. during crimping. After crimping some recoil is expected. It is expected that, in general, the initial diameter reduction can, within a reasonable approximation, be determined from the type of scaffolding pattern present. For the scaffolding pattern depicted in FIG. 3 it was found that a 60% reduction worked well.

It is believed that an initial diameter reduction of between about 55 to 65% from a starting diameter can produce noticeable differences in the amount of cracking/peeling in the coating for a polymer scaffolding having a closed cell pattern, e.g., FIG. 3. However, as explained earlier, this diameter reduction step, alone, may not produce acceptable results. Results can vary depending on the nature of the scaffolding pattern, coating composition, method of application of the coating, and method for crimping as discussed earlier.

It will be appreciated in view of this disclosure that in order to prevent, or cure a cracking/peeling problem in a more consistent manner, the scope of investigation cannot be confined to a diameter reduction step before coating. Unfortunately, the inventors found that the complexities associated with a fracture problem in a polymer-drug coating on a polymer scaffolding do not lend themselves to such an easy answer. In accordance with this aspect of invention, a method for increasing fracture resistance therefore includes, not only a diameter reduction step of about 50-80%, but also a diameter reduction for a polymer scaffolding, e.g., one having a closed cell pattern and strut displacement between crimped and deployed diameters as explained above in connection with FIGS. 2-4, a coating process including depositing a drug-polymer mixed with a solvent in an amount of between about 90-98% by weight solvent, an annealing step of about 15-60 min at a relaxation temperature of about 5-20 degrees below a glass transition temperature for an amorphous and semi crystalline polymer, and a crimping process including a three part diameter reduction at a relaxation temperature of between 5-20 degrees below a glass transition temperature for an amorphous polymer (coating) and semi crystalline polymer (scaffolding).

"Relaxation temperature" is intended to mean a temperature, relatively close to the glass transition temperature for the polymer, e.g., within 10 to 20 degrees of the glass transition temperature, which relieves internal stresses/strain induced by a deformation or working of the material when the material is subjected to this elevated temperature for a sufficient amount of time. The closer to, and above the glass transition temperature the more rapidly this relaxation process takes place. If the polymer is subjected to the relaxation temperature for too long, then the orientation in the structure begins to break down, which weakens the material. A "relaxation period" is intended to mean the period of time at which the polymer is subjected to a relaxation temperature and which has the effect of relieving internal stresses in the material.

With the stent body now at about 60% of its maximum diameter, the desired coating weight is applied by a spray coating process. Examples of a spray coating process are described in U.S. Publication Nos. 2009/0087541 and 2007/0281073. Preferably, and in accordance with some aspects of invention, a coating process includes.

After the spraying-drying cycle is complete, the stent is preferably placed within an oven to remove any remaining solvent. According to one aspect of invention, this baking step, originally intended for the purpose of boiling-off solvent following the spray-dry steps, might also increase the fracture resistance of the drug-eluting polymer stent. The prolonged exposure to the relaxation temperature during bake after the spray-dry process relieves internal stresses in the polymer-drug layer, scaffolding, and transition, intermediate or binding layer (as discussed earlier). The baking cycle is between 15 and 60 minutes at between 40-50 degrees Celsius. More generally, the baking temperature may be about 5-20 degrees C. below the glass transition temperature, and the duration will be chosen so that no degrading occurs in the mechanical properties of the load-bearing scaffolding.

Referring to FIG. 1, after the final dry weight for the PDLA-drug coating is achieved, a crimping process is applied to the coated stent using any suitable crimping machine. In one embodiment, the coated stent having the reduced diameter is crimped according to the four-stage process depicted in FIG. 1.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A method for making a medical device, comprising:
   using a scaffold comprising a polymer; and
   using a crimping device, crimping the scaffold from a first diameter to a second diameter by plastic deformation of the scaffold wherein
   during the crimping the scaffold has an elevated temperature of between 5 to 20 degrees below a glass transition temperature of the polymer, the scaffold is crimped to a balloon having a deployed diameter that is between 2 to 5 times the second diameter, the scaffold has a closed cell pattern formed by rings, wherein a ring comprises a first strut and a second strut adjoined at a hinge element, and the first strut displaces more than 130 degrees relative to the second strut when the scaffold is crimped from the first diameter to the second diameter.

2. The method of claim 1, wherein the scaffold is made from a tube.

3. The method of claim 1, wherein the scaffold polymer is PLLA or PLGA.

4. The method of claim 1, wherein the deployed diameter is about 3 times the second diameter.

5. The method of claim 1, wherein the crimping includes a first diameter reduction, followed by a second diameter reduction, wherein following the first diameter reduction the scaffold diameter is between 55% and 65% of the first diameter.

6. The method of claim 1, wherein the glass transition temperature of the polymer is the glass transition temperature of an amorphous polymer.

7. The method of claim 6, wherein the amorphous polymer is PDLA and the crimping temperature is 40 Deg. C.

8. A method for making a balloon-expanded medical device having increased fracture resistance, comprising:

using a scaffold comprising a polymer including a closed cell pattern formed by a pair of adjacent rings, each ring comprising a first strut and a second strut adjoined at a hinge element, the scaffold having a pre-crimp diameter;

depositing a coating on a surface of the scaffold including repeating the steps of depositing a drug-polymer mixed with a solvent in an amount of between about 90-98% by weight solvent until a final coating weight is reached; and crimping the scaffold to a balloon and a final crimp diameter while the scaffold has an elevated temperature of between 5 to 20 degrees below a glass transition temperature of the polymer, wherein the first strut rotates through an angle of more than 130 degrees relative to the second strut when the scaffold is crimped to the final crimp diameter.

9. The method of claim 8, wherein the crimping is performed using a mechanical crimper, the crimping including the steps of:

a) crimping the scaffold from the pre-crimp diameter to a first diameter;

b) maintaining the scaffold at the first diameter for a first relaxation period;

c) crimping the scaffold from the first diameter to a second diameter;

d) maintaining the scaffold at the second diameter for a second relaxation period;

e) crimping the scaffold from the second diameter to the final crimp diameter; and f) maintaining the scaffold at the final crimp diameter for a final relaxation period.

10. The method of claim 8, wherein the crimping is performed using a mechanical crimper, and wherein after the scaffold has been crimped to the final crimp diameter the scaffold final crimp diameter is maintained for a relaxation period within the mechanical crimper.

11. The method of claim 8, wherein the crimping includes a first diameter reduction, followed by a second diameter reduction, wherein the scaffold diameter is reduced in size by between 55% to 65% during the first diameter reduction, whereupon the scaffold diameter is maintained at the first diameter for a first relaxation period.

12. The method of claim 11, wherein following the second diameter reduction the scaffold is crimped to the final crimp diameter and held at the final crimp diameter for a second relaxation period.

13. The method of claim 10, wherein the scaffold is reduced to an ambient temperature during the relaxation period.

14. A method for making a medical device, comprising:

using a scaffold comprising a polymer; and using a crimping device, crimping the scaffold from a first diameter to a second diameter by plastic deformation of the scaffold, the crimping including at least a first and second diameter reduction of the scaffold, wherein during the crimping the scaffold has an elevated temperature of between 5 to 20 degrees below a glass transition temperature of the polymer, the scaffold first diameter is greater than a deployed diameter for the balloon, the scaffold has a closed cell pattern formed by a pair of adjacent rings comprising first and second struts adjoined at a hinge element, and a pair of links connecting the rings, and the first strut displaces more than 130 degrees relative to the second strut when the scaffold is crimped from the first diameter to the second diameter.

15. The method of claim 14, wherein the glass transition temperature of the polymer is the glass transition temperature of an amorphous polymer.

* * * * *